United States Patent [19]

Pletcher et al.

[11] Patent Number: 5,071,526

[45] Date of Patent: Dec. 10, 1991

[54] ACIDIC GAS SENSORS AND METHOD OF USING SAME

[75] Inventors: Derek Pletcher; John Evans, both of Romsey; Piers R. G. Warburton, Guernsey; Trevor K. Gibbs, Rayne, all of United Kingdom

[73] Assignee: Neotronics Technology PLC, Hertfordshire, United Kingdom

[21] Appl. No.: 199,426

[22] Filed: May 27, 1988

[30] Foreign Application Priority Data

May 28, 1987 [GB] United Kingdom .................. 8712582

[51] Int. Cl.[5] ...................... G01N 27/27; G01N 27/40
[52] U.S. Cl. ............................ 204/153.1; 204/153.14; 204/153.19; 204/400; 204/415; 356/326
[58] Field of Search ............... 204/1 T, 1 P, 400, 415, 204/153.1, 153.4, 153.19; 356/326-330

[56] References Cited

U.S. PATENT DOCUMENTS

| | | | |
|---|---|---|---|
| 3,227,643 | 1/1966 | Oklin et al. | 204/415 |
| 3,380,905 | 4/1968 | Clark | 204/415 |
| 3,719,576 | 3/1973 | Macur | 204/415 |
| 3,795,589 | 3/1974 | Dahms | 204/1 F |
| 4,263,115 | 4/1981 | Kessler et al. | 204/415 |
| 4,474,648 | 10/1984 | Tantram et al. | 204/415 |

FOREIGN PATENT DOCUMENTS

| | | |
|---|---|---|
| 1076403 | 6/1966 | Fed. Rep. of Germany . |
| 226655 | 8/1985 | German Democratic Rep. . |
| 834816 | 5/1960 | United Kingdom . |
| 2052755 | 1/1981 | United Kingdom . |
| 2094005 | 9/1982 | United Kingdom . |

OTHER PUBLICATIONS

"Hackh's Chemical Dictionary", 4th ed., 1969, p. 388.
*Nature*, vol. 218 (Apr. 1968), Bergman, "Metallized Membrane Electrode: Atmospheric Oxygen Monitoring and Other Applications," p. 266.
*J. Pure & Appl. Chem.*, vol. 36 (1973), Ross et al.; "Gas Electrodes-Potentiometric Gas Sensing Electrodes," pp. 473-487.
*Analytical Chemistry*, vol. 61, No. 6 (Mar. 1989), Evans et al., "Amperometric Sensor for Carbon Dioxide: Design, Characteristics and Performance," pp. 577-580.
*Analytical Chemistry*, vol. 59, No. 4 (Feb. 1987), Rios et al., "Electrochemical Determination of Sulfur Dioxide in Air Samples in a Closed-Loop Flow Injection System," pp. 666-670.
*Patent Abstracts of Japan*, vol. 7, No. 176 (P-214) [1321] Aug. 1983 relating to JP-A-58-079141.
*Industrial Gas Cleaning*, 2d ed., Strauss, "Basic Data Requirements," pp. 54-58.
*Ion-Selective Electrode Methodology*, vol. II, Riley, "Gas Sensing Probes," pp. 1-21.
*Chemical Detection of Gaseous Pollutants*, Ruch, pp. 50-54.
Severinghaus et al., "Electrodes for Blood $pO_2$ and $pCO_2$ Determination," Nov. 1958, pp. 515-520.
*Annals New York Academy of Sciences*, Severinghaus, "Measurements of Blood Gases: $PO_2$ and $PCO_2$," pp. 115-132.
*Analytical Chemistry*, vol. 51, No. 12, Oct. 1979, Jensen et al., "Response Time Characteristics of the $pCO_2$ Electrode," pp. 1972-1977.
*Analytical Chemistry*, vol. 57, No. 2, Feb. 1985, Czaban, "Instrumentation—Electrochemical Sensors in Clinical Chemistry: Yesterday, Today, Tomorrow," pp. 345A-356A.

(List continued on next page.)

*Primary Examiner*—T. Tung
*Attorney, Agent, or Firm*—Kerkam, Stowell, Kondracki & Clarke

[57] ABSTRACT

The present invention provides a sensor, preferably an electrochemical sensor, for detecting acidic gases, e.g. carbon dioxide. The electrochemical sensor has a sensing electrode (20, 22), a counter electrode (37) and a body of electrolyte containing a complex, e.g. copper-(II) bis(propanediamine), which has one or more ligands that is displaceable by the presence of the acidic gas in the electrolyte to form a modified complex which can be electrochemically reacted at the sensing electrode at a potential at which the unmodified complex is unreactive. The acidic gas diffuses into the electrolyte through a porous membrane. The modified complex can also be detected colorimetrically because it absorbs light at a different wavelength to the unmodified complex.

17 Claims, 3 Drawing Sheets

OTHER PUBLICATIONS

*Analytical Chemistry*, vol. 54, No. 12, Oct. 1982, Kobos, "Selectivity Characteristics of Potentiometric Carbon Dioxide Sensors with Various Gas Membrane Materials," pp. 1976-1980.

*Analytical Chemistry*, vol. 58, No. 8, Jul. 1986, Bruckenstein et al., "Continuous Conductometric Sensor for Carbon Dioxide," pp. 1766-1770.

*J. Chem. Soc.*, Faraday Trans. 1, vol. 1986, No. 82, Bruckenstein et al., "Analytical Applications of Gas Membrane Electrodes," pp. 1105-1116.

*Polarographic Oxygen Sensor*, Chap. 6, "Oxygen Tension Measurements in Gases," pp. 97-119.

*Measurement of Dissolved Oxygen*, Hitchman, "Membrane-Covered Polarographic Detectors—Introduction and Theory," pp. 59-63.

*J. Electrochem. Eng.*, 1977, Dietz et al.; "Electrochemical Sensors for the Analysis of Gases," pp. 1-90.

*Ann. Occup. Hyg.*, vol. 15, Pergamon Press 1972, Bergman et al., "Instruments Based on Polarographic Sensors for the Detection, Recording and Warning of Atmospheric Oxygen Deficiency and the Presence of Pollutants Such as Carbon Monoxide," pp. 329-337.

*Recording Blood $O_2$ Tension*, vol. 6, Clark, Jr. et al., "Continuous Recording of Blood Oxygen Tensions by Polarography," Sep. 1953, pp. 189-193.

*Ann. Occup. Hyg.*, vol. 18, Pergamon Press 1975, Bergman, "Electrochemical Carbon Monoxide Sensors Based on the Metallized Membrane Electrode," pp. 53-62.

*1985 IEEE*, Zook et al., "Nonaqueous Electrochemical Gas Sensors," pp. 326-329.

*J. Electroanal. Chem.*, vol. 138 (1982), Albery et al., "A Membrane Electrode for the Determination of $CO_2$ and $O_2$" pp. 79-87.

ACIDIC GAS SENSORS AND METHOD OF USING SAME

The present invention relates to a sensor for dissolved or gaseous carbon dioxide or other acidic gases, e.g. $SO_2$ and $NO_2$.

Carbon dioxide is an inert gas that is difficult to sense electrochemically because it reacts electrochemically only at high negative potentials and at such potentials, oxygen is reduced and water is decomposed. Thus it would be practically impossible to obtain an output current from a simple amperometric electrochemical sensor working with an aqueous electrolyte that is due solely to the reduction of carbon dioxide and in practice a substantial part of the sensor output current would be due to reduction of oxygen and/or decomposition of water and so the magnitude of the signal from the sensor would not be a direct measure of the amount of carbon dioxide present. Accordingly, presently used techniques for measuring carbon dioxide are (i) dissolution of the gas in a base and back-titration against an acid; (ii) infrared spectrometers tuned to the carbon dioxide absorption wavelength; (iii) potentiometric chemical sensors in which the gas sample under test is contacted with an aqueous solution in which carbon dioxide dissolves and the resulting lowering of pH is detected by a pH meter to give a measure of the amount of carbon dioxide in the test sample; and (iv) thermal conductivity.

These techniques have disadvantages: titration is slow and labour intensive; an infrared spectrometer for measuring gaseous carbon dioxide has to have a long path length between its infrared source and detector because the concentration of carbon dioxide molecules in the gas phase is low; such spectrometers are bulky and are not readily portable. Potentiometric chemical sensors have slow recovery times, that is to say there is a long delay before a reliable new output signal is generated after a sensor has been exposed to carbon dioxide. Furthermore, the output of the pH meter is logarithmic and it is relatively insensitive to concentrations of carbon dioxide towards the upper limit of the range that a sensor is designed for. Also, the range of carbon dioxide concentrations that can be measured by such sensors is limited and the output from the electrode of the pH meter is not as stable as is desirable.

An example of a potentiometric gas sensor using a hydrogen ion electrode (pH electrode) to measure the quantity of carbon dioxide in an atmosphere is described inter alia in an article by J. W. Ross et al in Journal of Pure and Applied Chemistry 36 (1973) pages 473–487.

Another approach to the electrochemical determination of carbon dioxide is described in U.S. Pat. Nos. 3,719,576 and 4,474,648. These patents describe sensors having a sensing electrode which comprises an electrochemical pH-sensitive couple, e.g. Ag/AgO, Pd/PdO or Ir/IrO and a counter electrode. When the pH of an electrolyte changes due to dissolution of carbon dioxide, the potential of the couple changes which results in a potential difference between the sensing and the counter electrodes causing a current to flow through the cell which can be detected by an external electric circuit. A similar method for detecting carbon dioxide is described in an article by Bergman in Nature, 218 (Apr. 20, 1968), page 266 in which a pH-sensitive, electrochemically-active material, e.g. quinhydrone or a bicarbonate, is dissolved in the electrolyte of an electrochemical cell having a sensing electrode, e.g. a platinum electrode, that can detect the potential of the material couple. Carbon dioxide can diffuse into the electrolyte through the sensing electrode, which is permeable, and this changes the potential of the material couple which is detected by the sensing electrode.

A still further approach to the problem of detecting carbon dioxide electrochemically is disclosed in GB 2,052,755 which describes a conductometric cell in which the conductivity between two measuring electrodes separated by an aqueous medium is measured by an external circuit; carbon dioxide is capable of diffusing through one of the electrodes and dissolving in the aqueous medium, thereby increasing the concentration of ions in the aqueous medium and so increasing the conductivity between the electrodes which is measured by the external circuit.

An electrochemical cell for detecting $SO_2$ and $NO_2$ is disclosed in U.S. Pat. No. 3,795,589 and has a sensing electrode and a body of electrolyte in contact with the atmosphere under test so that the gas to be detected can dissolve in the electrolyte. The electrolyte contains a redox system, e.g. a variable valency ion such as Cu(II) or Fe(III). The gas reduces the metal ion in the electrolyte and the reduced metal ion is re-oxidised to the original species at the working electrode and the amount of current required by the working electrode to restore the redox couple is a measure of the quantity of acidic gas in the fluid to be detected.

Despite the above proposals no commercially successful sensor working on amperometric principles has yet been produced.

The present invention is based on an entirely different approach which allows carbon dioxide to diffuse from a fluid under test into a solution of a metal complex whose ligands can be displaced by the presence of carbon dioxide (or other acidic gas) in the solution to form a modified complex which can be detected, e.g. electrochemically or by colorimetry, thereby providing a measure of the amount of carbon dioxide (or other acidic gas) in the fluid.

According to one aspect of the present invention there is provided an electrochemical sensor comprising a sensing electrode, a counter electrode and an intervening body of electrolyte that is accessible to the gas being tested, the electrolyte containing a metal complex having at least one ligand that can be displaced by the presence in the electrolyte of an acidic gas to form a modified complex, the system being such that the modified complex is electrochemically detectable at the sensing electrode at a potential at which the unmodified complex is electrochemically unreactive and which is above the potential at which oxygen is electrochemically reduced.

Thus, when carbon dioxide (or other acid gas) is present in the fluid being monitored, it diffuses into the electrolyte where it dissolves and leads to the displacement of one or more of the ligands in the complex and the modified complex thus produced is reacted electrochemically thereby generating a current in an external electric circuit which can be measured. The magnitude of the current gives a measure of the amount of gas in the fluid being sensed.

Without wishing to be committed to any particular theory for the mechanism of the change in the metal complex in the presence of carbon dioxide or other acidic gas, we postulate that the change in the metal complex may be brought about by the change in pH as a result of dissolution of the acidic gas in the solution of metal complex. Thus, for example, on dissolution of carbon dioxide, carbonic acid is formed according to reaction (1):

$$CO_2 + H_2O \rightarrow H^+ + HCO_3^- \qquad (1)$$

The change in pH alters the equilibrium between ligand molecules bound to the metal and ligand molecules bound to protons according to equation (2):

$$zH^+ + ML_n{}^{m+} \rightleftharpoons zHL^+ + ML_{(n-z)}{}^{m+} \qquad (2)$$

(where n, m and z are integers (although m can be zero), M is a metal and L is a ligand) and it is possible to detect the increase in the $ML_{(n-z)}{}^{m+}$ species or the decrease in the $ML_n{}^{m+}$ species; the magnitude of the disturbance of equilibrium (2) will give a measure of the amount of acidic gas present. In other words, the metal and hydrogen ions compete for binding to the ligand. Equation (2) is probably an over-simplification of the mechanism that actually takes place, and in particular the complex $ML_{(n-z)}{}^{m+}$ could well be stabilized by binding to further ligand(s).

For simplicity, in the present specification, a metal complex that is in its equilibrium (or unchanged) state (represented by the formula $ML_n{}^{m+}$ in equation (2) above) will be referred to simply as an "unmodified metal complex" whereas a complex that has undergone a change as a result of the presence of an acidic gas (represented by the formula $ML_{(n-z)}{}^{m+}$ in equation (2) above) will be referred to as a "modified metal complex".

It is preferred that the ligand is a base in the free state and it is particularly preferred if the ligand binds to the metal through a nitrogen atom, e.g. the ligands are chosen from amines, and diamines; other possible ligands include carboxylates, thiocarboxylates, phosphines, diphosphines, thiolates, oximes, amino acids, peptides, nucleotides, sugars, some alcohols, carbamates and thiocarbamates. Compounds having a basic nitrogen atom in a heterocyclic ring may also be used.

The metal and the ligands in the complex should be so chosen that the stability constant of the modified metal complex and the $pK_b$ of the ligand provides the optimum response to acidic gas in the range of acidic gas concentrations that it is desired to measure. It is desirable that the modified complex should be chosen so that it reacts electrochemically at a potential at which other species in the fluid being sensed do not react; in particular, when measuring the concentration of an acidic gas in an oxygen-containing atmosphere, it is desirable that the modified complex is such that it is reduced electrochemically at a potential that is sustantially more positive than that at which oxygen is reduced. It is envisaged that different metal complexes may be required to measure different concentrations of carbon dioxide. Preferred metals are variable valency metals having a stable lower oxidation state so that a complex of a reduced ion will be formed after reduction of the modified metal complex at the sensing electrode and this reduced ion complex will remain in solution; examples of possible metals are transition metals, for example Cu(II), Fe(III) and Ru(III); other possible metals are: Bi(III), Pb(II), Sn(IV), Pd(II), Ag(I), Os(III), Ir(III) and Mo(IV).

The ligands are preferably bidentate, e.g. diaminoalkanes, which can be optionally substituted on the alkyl chain, e.g. 1,3-propanediamine and ethylene diamine. Multidentate ligands having more than two binding sites can also be used.

The complex may be charged or neutral; preferred complexes are copper(II) bis-(1,3-propanediamine), copper(II) bis-(1,2-propanediamine), and copper bis-ethylenediamine which are all cations. When the complex is charged, the complimentary anion or cation should be chosen so that it does not adversely affect any other component of the sensor or any other species that may diffuse into the sensor together with the gas being sensed; for example, the complimentary ion may be chloride, bromide, sulphate, nitrate, perchlorate or tetrafluoroborate. The complimentary ion and/or the other ionic species present in the electrolyte, may, if the system permits, be used to stabilize the modified complex and/or the electrochemical reaction product of the modified complex by providing ligands for binding to the metal ion complex. Thus, for example, we have found that the copper(I) ions obtained by reducing the modified forms of the preferred copper(II) bis-(1,3-propanediamine) and copper (II)-bis(ethylenediamine) complexes are stabilized by chloride and bromide ions.

Any means can be used for detecting the modified metal complex that differentiates between the modified metal complex and the simple unmodified metal complex. However, we prefer to detect the complexes electrochemically.

In the presence of carbon dioxide (or other acidic gas), the preferred copper bis(propanediamine)$^{2+}$ complex in a chloride containing electrolyte (i.e. the complex in its modified form) is reduced at potentials below +0.3 volts (with respect to a standard calomel electrode) with a peak at +0.14 volts. In contrast, the copper complex in the absence of carbon dioxide (i.e. the unmodified metal complex) is only reduced at voltages negative to −0.3 volts with a peak at about −0.6 volts. Thus, by maintaining a potential of the sensing electrode in the range between +0.25 and 0 volts, e.g. +0.2 to +0.1 volts and preferably about +0.14 volts, the sensing electrode will reduce solely the modified copper complex and the resulting current at the sensing electrode will be proportional to the amount of carbon dioxide detected. Neither oxygen nor water is reduced within these ranges of potentials so that there is no interference from either of these substances in the output signal from the sensor. The optimum potential at which the sensing electrode is held will depend on the nature of both the metal complex and the electrolyte but the reduction potentials of any metal complex can readily be ascertained by measuring the current-potential curves of the complex in two separate tests, one being conducted in the presence of carbon dioxide (or other acidic gas) and the other in the presence of an inert gas, e.g. nitrogen.

All the potentials given in this specification are the potentials of the sensing electrode of a sensor with respect to a notional standard calomel reference electrode (SCE).

It is preferred that the products of the electrochemical reaction, which will generally be electrochemical reduction, of the metal complex should be an electrolyte-soluble species so that the sensing electrode is not changed by deposition of metal resulting from reduction of the complex to the metal; this requires that the metal ion in the complex is reducible to a stable lower oxidation state. However, it may still be possible to operate the sensor if the metal is deposited on the working electrode. The preferred couples are: Cu(II)/Cu(I), Fe(III)/Fe(II) and Ru(III)/Ru(II).

In the case of electrochemical reduction, the modified metal complex should have a reduction potential that is greater (i.e. more positive or less negative) than the reduction potential of the unmodified metal complex. Ideally the reduction potential of the modified metal complex should fall within the range of +0.5 to 0.0 volts (with respect to a standard calomel electrode) so as to minimise interfering side reaction, e.g. reduction of oxygen or the oxidation of other atmospheric components.

A membrane may be placed between the solution of the metal complex and the fluid being sensed to prevent escape of the electrolyte; the membrane can be porous or semi-permeable and, if the fluid being sensed contains any species (other than the toxic gas being sensed) which causes the above-mentioned change in the metal complex or which itself reacts electrochemically at the sensing electrode, a selective membrane can be chosen so as to block the passage of the interfering species. Interfering species can alternatively be blocked by providing a body of material, e.g. a filter, between the fluid being sensed and the sensing electrode that selectively absorbs or adsorbs the interfering species. If it is desired to sense carbon dioxide, then other acidic gases, e.g. sulphur dioxide or nitrogen dioxide, will interfere with the measurement but these gases can be absorbed on a suitable filtering material before they come into contact with the metal complex; this is relatively simple because carbon dioxide is inert compared to other acidic gases. Suitable filtering materials include, e.g. potassium permanganate, which absorbs sulphur dioxide, or activated charcoal which absorbs other active gases, e.g. $NO_2$, $Cl_2$ and ozone.

The membrane between the fluid being sensed and the complex-containing electrolyte is preferably part of the sensing electrode one side of which is in contact with the fluid being measured and the other with the electrolyte; the gas can then diffuse through the sensing electrode to the electrolyte. Membrane electrodes of this type are well known e.g. from U.S. Pat. No. 3,787,308 and an article by Niedrach et al, J. Electrochem. Soc. 112 (2), 117, 1965. Such electrodes generally consist of a layer of porous hydrophobic material, e.g. PTFE (polytetrafluoroethylene), facing the fluid under test and a layer of catalyst, e.g. platinum, on the electrolyte side of the electrode. In such an electrode, the gas diffuses through pores in the PTFE layer and comes into contact with the electrolyte where the carbon dioxide dissolves in the electrolyte. The rate at which the gas being measured diffuses to the electrolyte depends (inter alia) on the porosity and thickness of the PTFE layer and the amount reaching the electrolyte can be controlled by varying the thickness and/or porosity of the PTFE layer. In this way, the sensor can be tailored to detect a particular range of acidic gas concentrations by setting the porosity and/or thickness of the PTFE layer so that the amount of gas reaching the electrolyte is not greater than the sensing electrode can cope with. High ranges of gas concentrations can be detected by making the PTFE layer less porous and/or thicker and low concentrations by making the PTFE more porous and/or thinner. Instead of adjusting the porosity and/or thickness of the PTFE layer, a throttling orifice may be placed in front of the electrode to reduce the rate of flow of gas to the sensing electrode as is known in the art.

The metal complex will generally be dissolved in an aqueous solvent that also contains an inert current-carrying species, e.g. a solution of sodium- or potassium-chloride, -bromide, -perchlorate, -nitrate or -sulphate. We have found that non-aqueous solvents, e.g. methanol, will also function satisfactorily although this might be due to the presence of minute traces of water in the methanol. The use of non-aqueous solvents could provide a useful mechanism for minimising cross-sensitivity from other species, e.g. water, that may also be reduced at the sensing electrode and in certain circumstances, the difference between the potential at which the modified metal complex is reduced and the potential at which an interfering species or the unmodified complex is reduced can be adjusted to minimize the interference.

The sensing electrode we have used is a platinum or carbon electrode, but it is also possible to use sensing electrodes made of other materials, e.g. zinc, silver, gold or palladium, or a mixture of materials may be used. It can be advantageous to use a sensing electrode made of the same metal that is present in the complex so that the effect of the metal being deposited on the sensing electrode can be minimised.

The sensor may be of the known galvanic type with a consumable counter electrode, the counter electrode material being chosen to give the desired potential at the sensing electrode. Alternatively, the sensor may be of the polarographic (or voltametric) type in which the potential of the sensing electrode is imposed by an external circuit, for example of the type described in British Patent Specification 1,101,101. The sensor may then have two or three electrodes, the third electrode being a reference electrode, but generally a reference electrode is not necessary when the polarisation of the sensing electrode is small, e.g. when the fluid being sensed contains less than 5% carbon dioxide (or other acidic gas). The preferred reference electrode is a silver/silver chloride electrode.

The electrochemical sensor of the present invention has a faster recovery time than the known potentiometric sensors described above, i.e. sensors using a pH electrode to measure pH of a liquid in contact with the test fluid. The output signal produced by the sensor of the present invention, although not linear, is more nearly linear than the potentiometric sensors discussed above and therefore the sensors of the present invention are more sensitive to changes in acidic gas concentration than such potentiometric sensors.

We have also discovered that the preferred copper (II) complexes with amine ligands have a different absorption peak in the ultraviolet/visible part of the electromagnetic spectrum than the corresponding unmodified metal complex. This has lead to an alternative form of sensor which can simply consist of a body of the complex in a fixed or immobilized state and having access to the fluid (gas/liquid) to be sensed. The intensity and/or the colour of the complex will then give an approximate visual measure of the amount of carbon dioxide (or other acidic gas) present.

According to the present invention, there is provided a method of sensing the presence of carbon dioxide in a fluid, the method comprising contacting the fluid with a body a copper (II) complex having at least one amine ligand that is reversibly displaceable from the copper atom in the presence of carbon dioxide to form a modified copper complex and measuring the amount of the modified complex and/or the amount of the copper amine complex in the body to provide an indication of the quantity of carbon dioxide in the fluid.

According to another aspect of the present invention, there is provided a sensor for sensing carbon dioxide in a fluid, which sensor comprises:

a body accessible to carbon dioxide in the fluid, and containing a copper (II) complex having at least one amine ligand(s) which are reversibly displaceable from the copper atom in the presence of carbon dioxide to form a modified copper complex, means for detecting the increase in the concentration of the said modified copper complex and/or the decrease in the concentration of the said copper-amine complex and for providing a signal in accordance with the concentration of complex detected.

The detection means preferably comprises a source of electromagnetic radiation having a wavelength which is absorbed by the copper amine complex or by the modified complex, the source directing the radiation at the body, and a detector arranged to receive radiation of the said wavelength that has passed through the body, which detector gives an output signal in accordance with the amount of radiation received.

The copper amine complex is preferably copper (II) bis-(ethylenediamine) or copper (II) bis-(propanediamine).

The body containing the complex may be held in any matrix that will allow carbon dioxide to contact it. The matrix may be solid or semi-solid or it may be a liquid, i.e. a solvent. Access to the metal complex may be via a porous or semi-permeable membrane or the complex may be open to the fluid being sensed without the presence of an intervening membrane. The membrane can be of the type described above in connection with the electrochemical sensor. Also, a filter may be provided to remove interfering gases before they come into contact with the copper complex.

The sensor of the present invention (whether of the electrochemical type or the colorimetric type or indeed any other type) is preferably arranged to give an electrical output that can be analyzed by a monitor circuit to give a reading, in either digital or analog form, of the amount of carbon dioxide (or other acidic gas) in the fluid being sensed or it may provide a plot of the variation of the amount of carbon dioxide (or other acidic gas) with time; alternatively the monitor circuit may include an alarm that is triggered when the concentration of carbon dioxide (or other acidic gas) reaches a pre-set threshold value.

Two electrochemical sensors and a colorimetric sensor all of which are in accordance with the present invention will now be described, by way of example only, with reference to the accompanying drawings in which.

Figure 1:
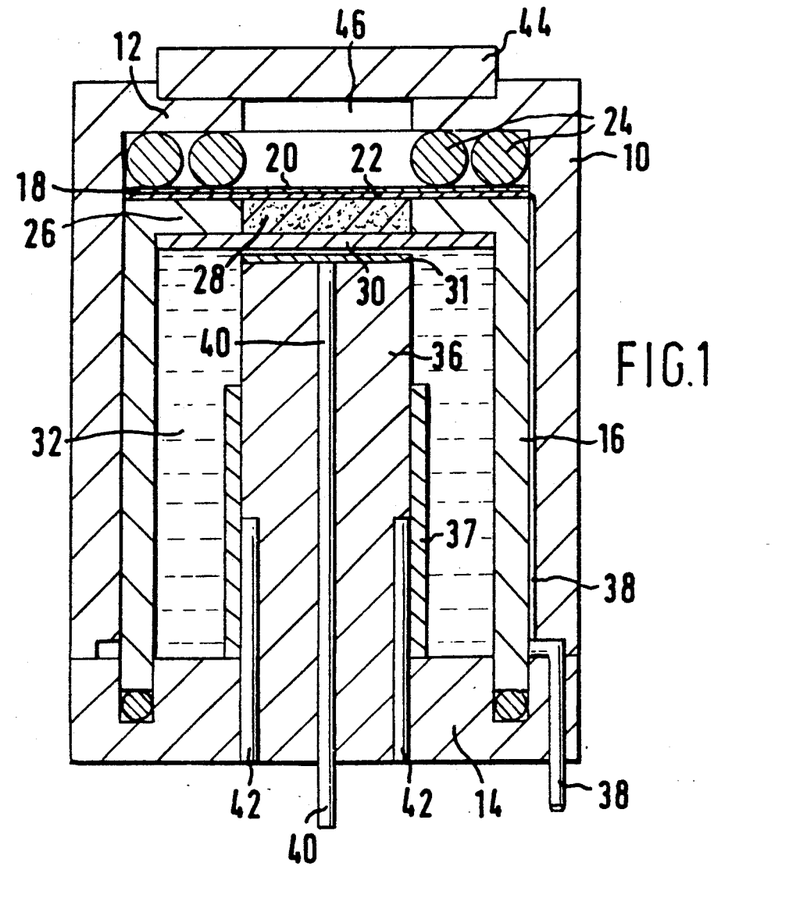
FIG. 1 is a cross-sectional view of an electrochemical sensor according to the present invention.

The sensor shown in FIG. 1 has a cylindrical outer housing 10 having a flange 12 at one end; the other end of the housing is sealed by a bottom plate 14 that is ultrasonically welded to housing 10. An internal housing 16 is located within outer housing 10 and supports a sensing diffusion electrode 18 which has a membrane 20 made of permeable or microporous polytetrafluoroethylene (or other hydrophobic material) facing flange 12 and a layer of catalyst 22, e.g. porous carbon, gold, platinum or palladium, bonded onto the face of the membrane 20 remote from the flange 12. Membrane 20 prevents evaporation of electrolyte from within the sensor while allowing ready access of carbon dioxide to the interior of the sensor. The space between electrode 18 and flange 12 is sealed by a pair of O rings 24. The top of the inner housing 16 also has a flange 26 defining an orifice and this is filled with highly absorbent material 28 saturated with electrolyte, which is a solution of 3 mM copper (II) bis(1,3-propanediamine) in 1M potassium chloride. An absorbent separator 30 is in contact with the inside face of flange 26 and can be made, e.g. from filter paper; a reservoir 32 of electrolyte is held within the body and keeps the separator 30 and material 28 saturated with electrolyte.

A silver wire 31 forming a silver/silver chloride reference electrode is in contact with the separator and is supported by a central column 36. An annular secondary (or counter) electrode 37 surrounds the base of column 36. Electrical contact to the three electrodes is provided by leads 38, 40 and 42.

Finally, an external filter 44 is provided covering the orifice 46 surrounded by flange 12 which prevents dust from entering the sensor and also protects the sensing electrode 18 from physical damage. Filter 44 can include material, e.g. potassium permanganate and/or activated charcoal, to remove interfering gases, e.g. $SO_2$, $NO_2$, $Cl_2$ and ozone.

The current may be detected by any known circuit to provide a reading of the amount of carbon dioxide sensed and hence the amount of carbon dioxide in the fluid. For example, the circuit may simply consist of an ammeter, e.g. a resistor connecting the sensing and the counter electrodes together and a voltmeter in parallel with the resistor, or, when using a reference electrode, the circuit may be as described in British Patent Specification 1,101,101 or 1,372,245.

Carbon dioxide diffuses through the membrane 20 with a flux proportional to the amount of carbon dioxide in the fluid under test; the carbon dioxide causes the copper complex to change into the modified copper complex $CuCl_4^{2-}$. The catalyst layer 23 of the sensing electrode is held at a potential of about $+0.15$ V with respect to a standard calomel electrode (approximately $+0.20$ with respect to the silver/silver chloride reference electrode), at which potential the modified copper complex ($CuCl_4^{2-}$) is reduced but the unmodified copper bis-(1,3-propanediamine) complex is not. The electrochemical reduction of the modified copper complex causes a current to flow between the sensing electrode 18 and the counter electrode 37 which is proportional (although not linearly proportional) to the amount of carbon dioxide that has passed through the membrane and so the current is proportional to the amount of carbon dioxide in the fluid under test.

Figure 2:
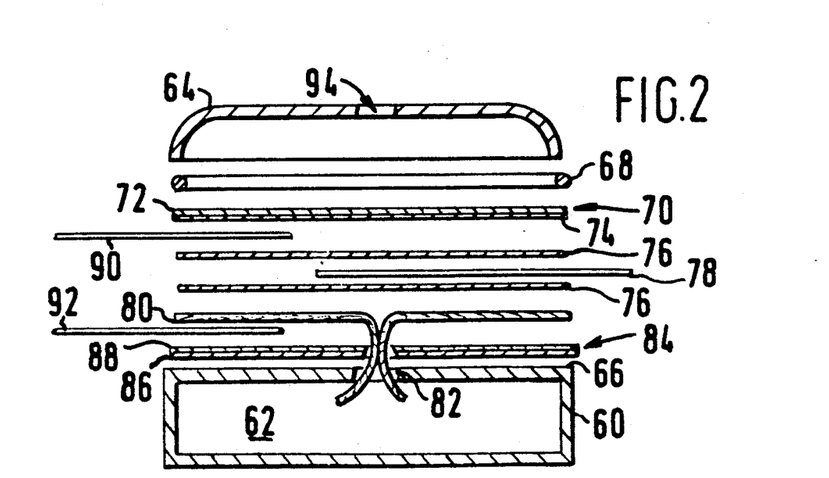
FIG. 2 is a schematic exploded cross-sectional view of further electrochemical sensor according to the present invention.

A second electrochemical sensor is shown in a schematic exploded section in FIG. 2 and includes a housing 60 enclosing a reservoir 62 for electrolyte and top plate 64 which in the operational sensor is secured against the top surface 66 of the housing 60 by bolts (not shown); an O-ring 68 ensures the seal between the housing and the top plate. In the space between the top plate and the housing, there is arranged the following:

a sensing electrode 70 composed of a sheet of porous polytetrafluoroethylene 72 on the underside of which there is a layer 74 of catalyst, e.g. platinum or carbon which has been sprayed onto the PTFE sheet 72, two layers of insulating absorbent material 76, e.g. filter paper, a silver wire 78 constituting the reference electrode, a wick 80 composed of highly absorbent insulating material, e.g. glass fibre paper, a portion of which extends into the reservoir through a hole 82 in the top surface of the housing, a counter electrode 84 through which the wick 80 extends and which is composed of a sheet 86 of PTFE on the top surface of which there is applied a layer 88 of catalyst, e.g. platinum or carbon, and platinum current collectors 90 and 92 in contact with the catalyst layers 74, 88, which extend outwards from the housing to provide terminals for connection to a detection circuit.

When the top plate 64 is clamped against housing 60, the edges of the PTFE layers 72,86 are compressed between the O-ring 68 and the housing, thereby producing a liquid-tight seal. The reservoir 62 is filled with electrolyte which is an aqueous solution of 3 mM copper (II) bis(1,3-propanediamine) in 1M KCl; the electrolyte is drawn by capillary action by the wick 80 to saturate material 76 with electrolyte. Because PTFE is hydrophobic, the electrolyte cannot escape through the electrode 70 but gas can diffuse through it. In operation, carbon dioxide diffuses from the atmosphere being sensed through an orifice 94 in the top plate 64, through the pores in the PTFE sheet 72 and through the layer of catalyst to dissolve in the electrolyte, where it causes the copper (II) complex to change to its modified form which is reduced at the sensing electrode 70 and this causes a current to flow through the sensor. The current collectors 90,92 and reference electrode 78 are connected to an external circuit as discussed above in connection with FIG. 1 to maintain the potential of the sensing electrode at +0.015 V (vs SCE) and to detect the current flowing through the sensor and hence the amount of carbon dioxide in the atmosphere.

Figure 3:
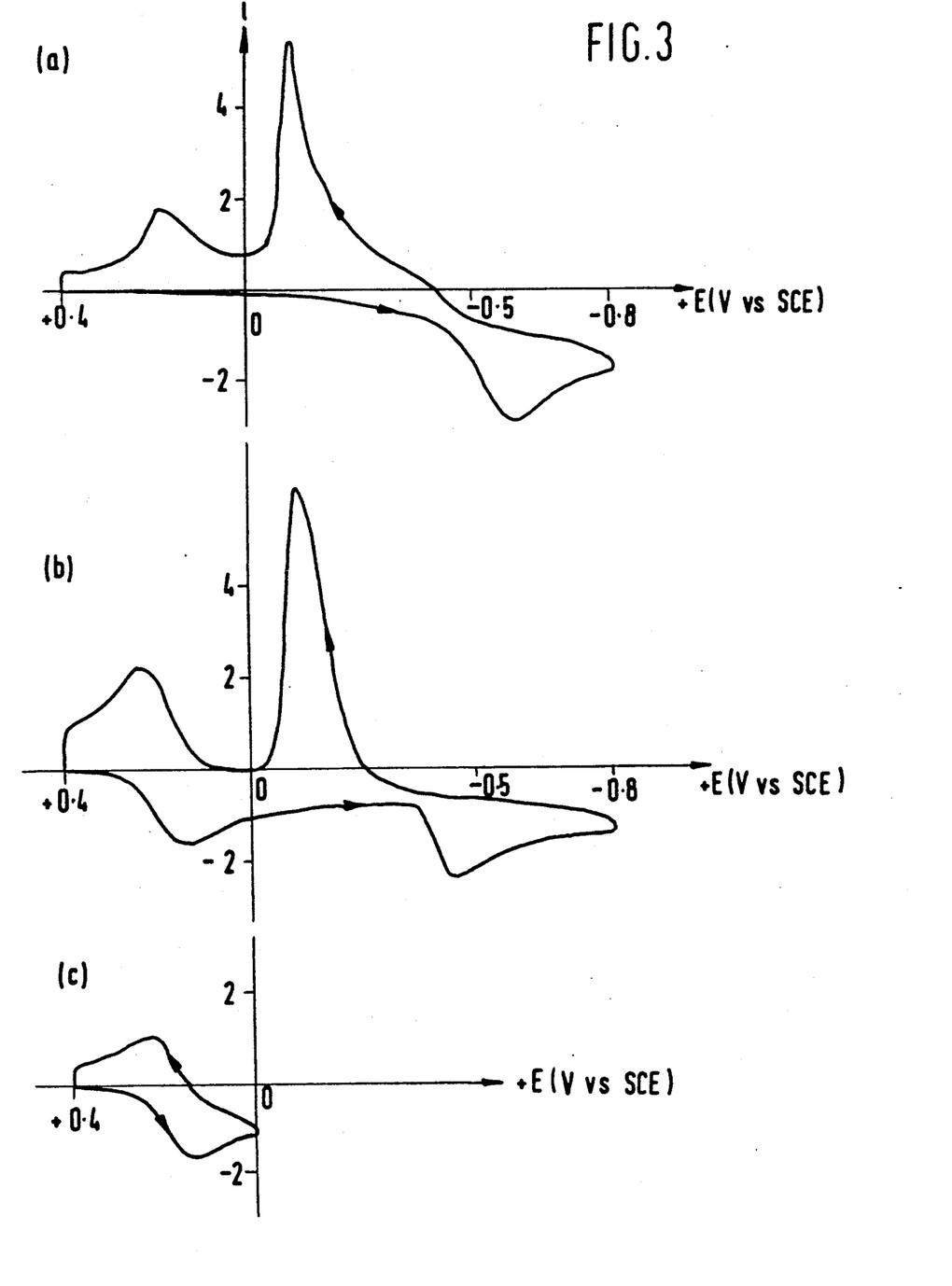
FIG. 3 shows three cyclic voltammograms measuring the current in $\mu A$ vs applied voltage (with respect to a SCE) of copper (II) bis-(1,3-propanediamine), plot a) being conducted under a nitrogen atmosphere and plots b) and c, being under a carbon dioxide atmosphere.

FIG. 3 shows a cyclic voltammogram for a solution of 2.8 mM copper (II) (bis-(1,3-propanediamine) in 1M potassium chloride. The working electrode is a polished vitreous carbon disc with a potential scan rate of 0.3 V/s. FIG. 3(a) shows the cyclic voltammogram of the solution when degassed with nitrogen; with this electrolyte the diamine complex gives a single, irreversible reduction peak at $-0.59$ V and it is likely that this results from the reduction of Cu(II) to Cu(0).

FIG. 3(b) shows the cyclic voltammogram after the solution has been saturated with carbon dioxide. The reduction of copper(II) now takes place in two stages with peaks at $+0.15$ V and $-0.46$ V. Thus the first reduction process is observed at a potential ($+0.15$ V) where little interference from oxygen reduction is to be expected and is probably due to the reduction of Cu(II) to Cu(I). Indeed, passing oxygen through the solution does not affect this part of the voltammogram. The Cu(II)/Cu(I) couple is close to reversible as shown by FIG. 3(c). The chemical change on passing carbon dioxide through the solution appears to be:

$$Cu(NH_2(CH_2)_3NH_2)_2{}^{2+} + 4H^+ + 4Cl^- \rightleftharpoons CuCl_4{}^{2-} + 2NH_3{}^+(CH_2)_3NH_3{}^+ \qquad (3)$$

and the reduction peak at $+0.15$ V is due to the process:

$$CuCl_4{}^{2-} + e^- \rightleftharpoons CuCl_4{}^{3-} \qquad (4)$$

Passing carbon dioxide/nitrogen mixtures through the solution led to voltammograms intermediate between those of FIGS. 3(a) and 3(b) and the changes in voltammetry could be cycled by passing nitrogen and carbon dioxide alternately indicating that reactions (3) and (4) are reversible.

Figure 4:
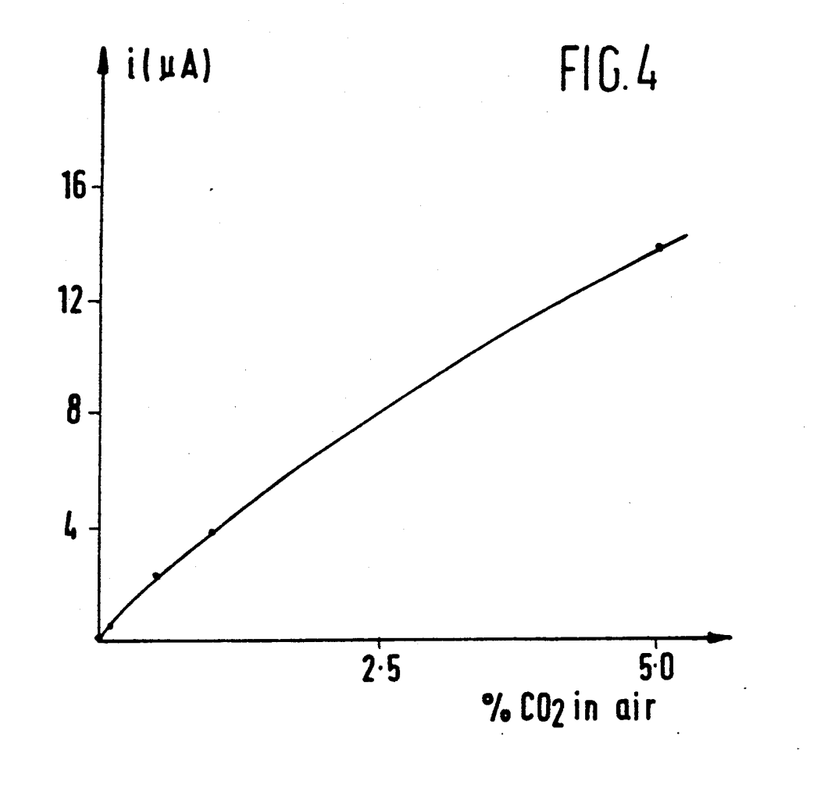
FIG. 4 is a plot of current (in $\mu A$) vs. percentage carbon dioxide content in air from a sensor of FIG. 2.

Thus by maintaining the potential of the sensing electrode at +0.25 to 0 V (vs SCE), the modified complex $CuCl_4{}^{2-}$ will be reduced but the unmodified propanediamine complex will not. Since the amount of the modified $CuCl_4{}^{2-}$ complex in the electrolyte is dependent on the amount of carbon dioxide in solution, which in turn is dependent on the amount of carbon dioxide in the atmosphere being sensed, the current resulting from a sensor of the general design shown in FIGS. 1 or 2 in which the sensing electrode is held at +0.25 to 0 V (vs SCE), preferably +0.20 to +0.10, e.g. +0.15 V, is dependent on the amount of carbon dioxide in the atmosphere. This is shown in FIG. 4 which is a plot of current vs carbon dioxide content of an atmosphere using the sensor shown in FIG. 2; although the output of the sensor is not quite linear, the non-linearity can be taken into account in the electronic circuit monitoring the sensor output. The output curve is very much more sensitive to changing carbon dioxide concentrations in the atmosphere than known sensor using pH electrodes discussed in the introduction to the present specification. Also, it will be noted that no current flows when there is no carbon dioxide in the atmosphere. The response time of the sensor of FIG. 2, i.e. the time between carbon dioxide being introduced into an atmosphere being sensed and the appearance of a current in the external circuit is about 12 seconds and the recovery time for the current to return to zero when carbon dioxide is no longer present in the atmosphere is about 30 seconds.

The data from bromide solution was almost identical to that from chloride media except that the first reduction peak occurs at a slightly more positive potential, $Ep = +0.22$ V.

A cyclic voltammogram of copper(II) bis-(1,3-propanediamine) in a sodium perchlorate electrolyte gives a well-defined peak at $-0.12$ V (vs SCE) in the presence of carbon dioxide whereas in the absence of carbon dioxide the complex gives a reduction peak at $-0.46$ V. Although a sensor could be devised on this system by maintaining the potential of the sensing electrode at $-0.15$ V, this gives rise to some interference from oxygen. Furthermore, the reduction of the copper(II) complex in the presence of carbon dioxide is believed to result in Cu(0). Therefore, it is preferred to use an electrolyte containing chloride or bromide ions (in addition to the copper complex), resulting in the following advantages over the use of perchlorate electrolytes:

(a) the potential of the sensing electrode can be held at a potential greater of between +0.025 and 0 V (vs SCE), e.g. +0.2 to 0.1 V and preferably at +0.15 V, where interference from cathodic oxygen reduction is likely to be minimal, (b) the reductions of $CuCl_4^{2-}$ and $CuBr_4^{2-}$ are electrochemically reversible and therefore are unlikely to be affected by minor changes in the electrode surface, (c) in the halide media, the reduction of the copper (II) leads to solution stable copper(I) species and so avoids deposition of copper on the cathode which would lead to a change in the electrode area and irreversible, if slow, loss of copper(II) from solution, (d) the halide ion complexes the copper(II) as the diamine ligand is protonated and removed from the metal ion, which influences the equilibrium constant of reaction (3) in such a way that the diamine is removed at higher pH. Hence reaction (3) will shift to the right in the presence of lower carbon dioxide concentrations and the sensor will be sensitive to lower amounts of carbon dioxide in the atmosphere, (e) in chloride (and probably bromide media) oxygen slowly reconverts the copper(I) to copper(II). This was confirmed by passing air through a solution of copper (I) in 1M KCl formed by electrolysis. Hence in a sensor, the copper(II) concentration would be maintained constant by contact with air.

The behaviour of ethylenediamine is similar to that of 1,3-propanediamine except that the removal of the ethylenediamine from the copper(II) (reaction (3)) occurs at a lower pH and therefore the Cu(II)(bis-ethylenediamine) ion is only suited to a sensor intended for sensing high carbon dioxide concentrations.

When measuring gases that are more acidic than carbon dioxide, ligands having a lower $pK_b$ value than 1,3-propanediamine can be used to bring about reaction (3) above.

The concentration of the copper complex in solution was found to be important; if it is too high, a precipitate of what is believed to be copper hydroxide was observed in the presence of carbon dioxide. For this reason, the concentration of copper bis-(1,3-propanediamine) and copper bis(ethylenediamine) is preferably less than 5 mM, e.g. about 2-3 mM, for measuring 0-10% carbon dioxide.

Figure 5:
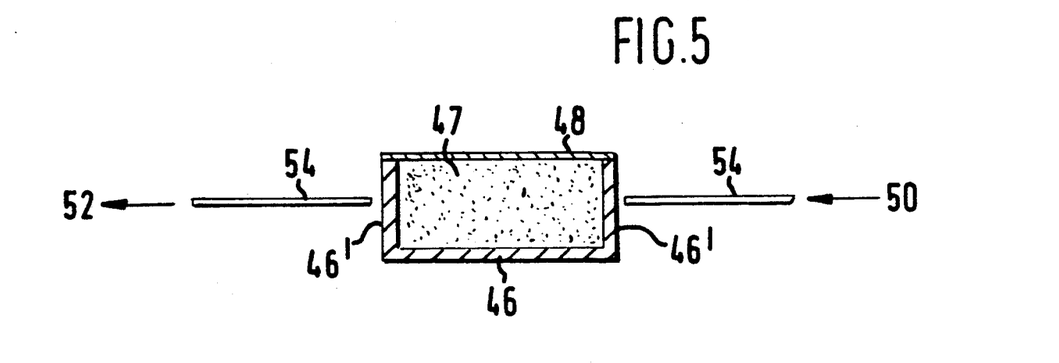
FIG. 5 is a schematic drawing of a colorimetric sensor of the present invention.

A colorimetric sensor for detecting carbon dioxide is schematically illustrated in FIG. 5. A vessel 46 having end faces 46′ is filled with an aqueous solution 47 of copper bis-(1,3-propanediamine) tetrafluoroborate in potassium chloride or sodium perchlorate. The vessel is covered with a hydrophobic porous PTFE membrane 48 that allows carbon dioxide to diffuse from a fluid being measured to the interior of vessel 46. If there is no carbon dioxide in the atmosphere being sensed the copper complex has a blue/purple colour having an absorption peak at 775 nm; in the presence of carbon dioxide, the copper complex changes to a light blue colour having an absorption peak at 556 nm (in the perchlorate medium) or colourless (in the chloride medium). The change in the copper complex in the presence of carbon dioxide can be detected by placing the vessel between the source and the detector of a visible/ultraviolet spectrometer. In a preferred embodiment, the light is conducted from the source 50 and to the detector 52 along optical fibres 54, which may be physically attached to the end faces 46′; such an arrangement allows the vessel 46 to be located away from the sensitive sensing parts of the spectrometer.

In the perchlorate medium, the source 50 and detector 52 can be tuned to either 775 nm or 556 nm (although the former is preferred because it is more sensitive to the detection of low levels of carbon dioxide) and the size of the output from the detector 52 will give a measure of the carbon dioxide that has migrated through the membrane 48 and therefore the amount of carbon dioxide in the fluid being sensed. The peaks at which the unmodified copper complex and the modified copper complex absorb are broad so that the exact wavelength of the radiation can be varied from the values given. The effect of carbon dioxide on copper bis-(1,3-propanediamine) is reversible and so when the concentration of carbon dioxide in the fluid being sensed drops the modified copper complex will revert to the unmodified copper complex.

We claim:

1. An electrochemical sensor for sensing the amount of an acidic gas in a fluid, the sensor comprising a sensing electrode, a counter electrode and an intervening body of electrolyte that is accessible to the gas being tested, the electrolyte containing a complex of a metal having at least one ligand selected from the group consisting of propane diamine and ethylene diamine that can be displaced by the presence in the electrolyte of an acidic gas to form a modified complex in which the metal has the same oxidation state as in the unmodified complex, the system being such that the modified complex is electrochemically detectable at the sensing electrode at a potential at which the unmodified complex is electrochemically unreactive and which is above the potential at which oxygen is electrochemically reduced.

2. A sensor as claimed in claim 1, wherein the sensing electrode comprises a layer of catalyst material supported on a layer of hydrophobic material, said hydrophobic material being in contact with the fluid being sensed and said layer of catalyst material being in contact with the electrolyte.

3. A sensor as claimed in claim 2, wherein the hydrophobic material is porous.

4. A sensor as claimed in claim 1, wherein the complex contains a metal ion selected from the group consisting of copper (II), iron (III) and ruthenium (III).

5. A sensor as claimed in claim 1, wherein the metal in the complex has two or more stable oxidation states so that, on reaction of the modified complex at the sensing electrode, the resulting product is soluble in the electrolyte.

6. A sensor as claimed in claim 1, wherein the electrolyte contains further ligands that can bind to the modified complex.

7. A sensor as claimed in claim 6, wherein the further ligands are chloride or bromide ions.

8. A sensor as claimed in claim 1, which includes means for maintaining the potential of the sensing electrode in the range of from 0 to 0.5 V with respect to a standard calomel electrode.

9. A sensor for sensing carbon dioxide in a fluid, which sensor comprises:
a body accessible to carbon dioxide in the fluid, and containing a copper (II) complex having at least one amine ligand(s), the ligand(s) being reversibly displaceable from the copper atom in the presence of carbon dioxide to form a modified copper complex in which the metal has the same oxidation state as in the unmodified complex; and
means for detecting the increase in the concentration of said modified copper complex and/or the decrease in the concentration of said copper-amine complex and for providing a signal in accordance with the concentration of complex detected.

10. A sensor as claimed in claim 9, wherein said amine ligand is an alkane diamine.

11. A sensor as claimed in claim 10, wherein the ligand is propane diamine or ethylene diamine.

12. A sensor as claimed in claim 9, wherein said body also contains further ligands that bind to the modified copper complex.

13. A sensor as claimed in claim 12, wherein the further ligands are chloride or bromide ions.

14. A sensor as claimed in claim 9, wherein the detecting means comprises a source of electromagnetic radiation at a wavelength which is absorbed by the copper amine complex or by the modified complex, the source directing the radiation at the body, and a detector arranged to receive radiation of said wavelength that has passed through the body, which detector gives an output signal in accordance with the amount of radiation received.

15. A sensor as claimed in claim 14, wherein the electromagnetic source and the detector are connected to the body by respective optical fibers.

16. A sensor as claimed in claim 9, wherein said amine ligand is a substituted alkane diamine.

17. A method of sensing the amount of carbon dioxide in a fluid, the method comprising contacting the fluid with a body containing a copper (II) complex having at least one amine ligand that, in the presence of carbon dioxide, is reversibly displaceable from the copper atom to form a modified copper complex in which the metal has the same oxidation state as in the unmodified complex, and measuring the amount of the modified complex and/or the amount of the copper amine complex in the body to provide an indication of the amount of carbon dioxide in the fluid.

* * * * *